(12) United States Patent
San et al.

(10) Patent No.: US 7,569,380 B2
(45) Date of Patent: Aug. 4, 2009

(54) SIMULTANEOUS ANAEROBIC PRODUCTION OF ISOAMYL ACETATE AND SUCCINIC ACID

(75) Inventors: Ka-Yiu San, Houston, TX (US); Ailen Sanchez, Houston, TX (US); George N. Bennett, Houston, TX (US); Cheryl Renee Dittrich, Houston, TX (US)

(73) Assignee: Rice University, Houston, TX (US)

( * ) Notice: Subject to any disclaimer, the term of this patent is extended or adjusted under 35 U.S.C. 154(b) by 435 days.

(21) Appl. No.: 11/315,453

(22) Filed: Dec. 22, 2005

(65) Prior Publication Data

US 2006/0141594 A1 Jun. 29, 2006

Related U.S. Application Data

(60) Provisional application No. 60/638,765, filed on Dec. 22, 2004.

(51) Int. Cl.
*C12N 1/20* (2006.01)
*C12N 5/00* (2006.01)
*C12N 5/02* (2006.01)

(52) U.S. Cl. .................. 435/252.3; 435/325; 435/383

(58) Field of Classification Search ........................ None
See application file for complete search history.

(56) References Cited

U.S. PATENT DOCUMENTS

| | | | |
|---|---|---|---|
| 6,159,738 | A | 12/2000 | Donnelly et al. |
| 6,448,061 | B1 | 9/2002 | Pan et al. |
| 6,455,284 | B1 | 9/2002 | Gokarn et al. |
| 7,223,567 | B2 | 5/2007 | Ka-Yiu et al. |
| 7,256,016 | B2 | 8/2007 | San et al. |
| 7,262,046 | B2 | 8/2007 | Ka-Yiu et al. |
| 2003/0087381 | A1 | 5/2003 | Gokarn et al. |
| 2004/0199941 | A1 | 10/2004 | San et al. |
| 2005/0196866 | A1 | 9/2005 | San et al. |
| 2006/0073577 | A1 | 4/2006 | Ka-Yiu et al. |
| 2006/0128001 | A1 | 6/2006 | Yukawa et al. |

FOREIGN PATENT DOCUMENTS

| | | |
|---|---|---|
| WO | PCT/US2006/037107 | 9/2006 |
| WO | WO 2007/001982 | 1/2007 |
| WO | PCT/US2007/077163 | 8/2007 |
| WO | PCT/US2007/077806 | 9/2007 |

OTHER PUBLICATIONS

Leonardo et al. (Anaerobic regulation of the adhE gene, Encoding the Fermentative Alcohol Dehydrogenase of *Escherichia coli* (Journal of Bactriology, Feb. 1993, vol. 175, No. 3 p. 870-878).*
U.S. Appl. No. 10/923,635, filed Aug. 20, 2004, San et al.
U.S. Appl. No. 10/987,511, filed Nov. 12, 2004, San et al.
Alam, K et al., "Anaerobic fermentation balance of E. coli as observed by in vivo nuclear magnetic resonance spectroscopy"; J. of Bacteriology, vol. 171(11), pp. 6213-6217, Nov. 1989.

Amann, et al., "Tightly regulated tac promoter vectors useful for the expression of unfused and fused proteins in Escherichia coli," Gene 69:301-15 (1988).
Chou, C., et al.; "Effect of Modulated Glucose Uptake on High-Level Recombinant Protein Production in a Dense E. coli Culture"; Biotechnol. Prog., vol. 10, pp. 644-647, 1994.
Dittrich, C. R.; Vadali, R. V.; Bennett, G. N.; San, K.-Y. "Redistribution of metabolic fluxes in the central aerobic metabolic pathway of E. coli mutant strains with deletion of the ackA-pta and poxB pathways for the production of isoamyl acetate" Biotechnol. Prog. 2005, 21, 627-631.
Fujii, T.; Nagasawa, N.; Iwamatsu, A.; Bogaki, T.; Tamai, Y.; Hamachi, M. "Molecular cloning, sequence analysis, and expression of the yeast alcohol acetyltransferase gene". Appl Environ Microbiol. 1994, 60, 2786-2792.
Gokarn, R. R.; Eiteman, M. A.; Altman, E., "Expression of pyruvate carboxylase enhances succinate production in Escherichia coli without affecting glucose uptake rate",. Biotech. Let. 1998, 20, 795-798.
Gokarn, R. R.; Eiteman, M. A.; Altman, E., "Metabolic analysis of Escherichia coli in the presence and absense of the carboxylating enzymes phosphoenolpyruvate carboxylase and pyruvate carboxylase",. Appl Environ Microbiol. 2000, 666, 1844-1850.
Hahm, D. H.; Pan, J. G.; Rhee, J. S., "Characterization and evaluation of a pta (Phosphotransacetylase) negative mutant of Escherichia coli HZB101 as a production host of foreign lipase",. Appl Microbiol Biotechnol. 1994, 42, 100-107.
Hari Krishna, S.; Divakar, S.; Prapulla, S. G.; Karanth, N. G. "Enzymatic synthesis of isoamyl acetate using immobilized lipase from Rhizomucor miehei",. J Biotechnol. 2001, 87, 193-201.
Holms, W. H. "The central metabolic pathways in Escherichia coli: relationship between flux and control at a branchpoint, efficiency of conversion to biomass, and excretion of acetate",. Curr Top Cell Regul. 1986, 28, 69-105.
Hong, S. H.; Lee, S.-Y. "Importance of redox balance on the production of succinic acid by metabolically engineered Escherichia coli",. Appl Microbiol Biotechnol. 2002, 58, 286-290.
Horton, C. E.; Huang, K. X.; Bennett, G. N.; Rudolph, F. B. "Heterologous expression of the Saccharomyces cervisiae alcohol acetyltransferase",. 2003.
Kern, et al., "Isoamyl alcohol-induced morphological change in Saccharomyces cerevisiae involves increases in mitochondria and cell wall chitin content," FEMS Yeast Res. 5:43-9 (2004).

(Continued)

*Primary Examiner*—Jon P Weber
*Assistant Examiner*—Kagnew H Gebreyesus
(74) *Attorney, Agent, or Firm*—Baker & McKenzie LLP

(57) ABSTRACT

In vivo method of producing esters from acetyle coA, such as isoamyl acetate and succinate, has been developed by producing null mutants in pathways that use acetyl coA and by overexpressing products that use NADH and in order to maintain the proper redox balance between NADH and NAD+. The method is exemplified with null mutations in ldhA, adhE, ackA-pta and overexpression of pyruvate carboxylase and alcohol acetyltransferase. This strain produces higher levels of both isoamyl acetate and succinate.

11 Claims, 4 Drawing Sheets

OTHER PUBLICATIONS

Kornberg, H. L. "*The role and control of the glyoxylate cycle in Escherichia coli*" Biochem. J. 1966, 99, 1-11.

Leonardo, M. et al., Anaerobic regulation of the adhE gene, encoding the fermentative alcohol dehydrogenase of *E. coli*; J. of Bacteriology, vol. 175(3), pp. 870-878, Feb. 1993.

Levanon SS, San KY, Bennett GN., "*Effect of oxygen on the Escherichia coli ArcA and FNR regulation systems and metabolic responses*", Biotechnol Bioeng. Mar. 5, 2005;89(5):556-64.

Lin H, Vadali RV, Bennett GN, San KY., *Increasing the acetyl-CoA pool in the presence of overexpressed phosphoenolpyruvate carboxylase or pyruvate carboxylase enhances succinate production in Escherichia coli*,. Biotechnol Prog. Sep.-Oct. 2004;20(5):1599-604.

Luli, G. W.; Strohl, W. R. "*Comparison of growth, acetate production, and acetate inhibition of Escherichia coli strains in batch and fed-batch fermentations*" Applied and Environmental Microbiology. 1990, 56, 1004-1011.

Maicas, S et al., "*NAD(P)H regeneration is the key for heterolactic fermentation of hexoses in Oenococcus oeni*" Microbiology, Jan. 2002;148(Pt 1):325-32.

Nagasawa, N.; Bogaki, T.; Iwamatsu, A.; Hamachi, M.; Kumagai, C. "*Cloning and nucleotide sequence of the alcohol acetyltransferase II gene (ATF2) from Saccharomyces cerevisiae*", Biosci. Biotech. Biochem. 1998, 62, 1852-1857.

Park, D. et al., "*Utilization of electrically reduced neutral red by Actinobacillus succinogenes: physiological functio of neutral red in membrane-driven fumarate reduction and energy conservation*"; J. of Bacteriology, vol. 181(8), pp. 2403-2410, Apr. 1999.

Phillips, G. J.; Park, S. K.; Huber, D. "*High copy number plasmids compatible with commonly used cloning vectors*". Biotechniques. 2000, 28, 400-408.

Sanchez, et al., "*Efficient succinate production from glucose through overexpression of pyruvate carboxylase in an E. coli alcohol dehydrogenase and lactate dehydrogenase mutant*," Biotechnol. Prog. 21:358-65 (2005).

Sanchez, et al., "*Novel pathway engineering design of the anaerobic central metabolic pathway in E. coli to increase succinate yield and productivity*," Metab. Eng. 7:229-39 (2005).

Vadali RV, Bennett GN, San KY., "*Cofactor engineering of intracellular CoA/acetyl-CoA and its effect on metabolic flux redistribution in Escherichia coli*". Metab Eng. Apr. 2004;6(2):133-9.

Vadali RV, Bennett GN, San KY., "*Enhanced isoamyl acetate production upon manipulation of the acetyl-CoA node in Escherichia coli*". Biotechnol Prog. May-Jun. 2004;20(3):692-7.

Vadali RV, Horton CE, Rudolph FB, Bennett GN, San KY., "*Production of isoamyl acetate in ackA-pta and/or ldh mutants of Escherichia coli with overexpression of yeast ATF2*". Appl Microbiol Biotechnol. Feb. 2004;63(6):698-704. Epub Oct. 28, 2003.

Vadali, R. V.; Bennett, G. N.; San, K.-Y., "*Applicability of CoA/acetyl-CoA manipulation system to enhance isoamyl acetate production in Escherichia coli*". Metabolic Engineering. 2004a, 6, 294-299.

Vemuri, G. N.; Eiteman, M. A.; Altman, E., *Effect of growth mode and pyruvate carboxylase on succinic acid production by metabolically engineered strains of Escherichia coli*. Appl Environ Microbiol. 2002, 68, 1715-1727.

Yoshimoto, H.; Fujiwara, D.; Momma, T.; Tanaka, K.; Sone, H.; Nagasawa, N.; Tamai, Y., "*Isolation and classification of the ATF2 gene encoding alcohol acetyltransferase II in the bottom fermenting yeast Saccharomyces pastorianus*" Yeast. 1999, 15, 409-417.

Yoshioka, K.; Hashimoto, N., "*Ester formation by alcohol acetyltransferase from brewers' yeast*". Agric Biol Chem. 1981, 45, 2183-2190.

\* cited by examiner

Isoamyl Acetate Production with Isoamyl Alcohol Variation

Extracellular Metabolites for SBS990MG(pHL413) with Isoamyl Alcohol and Variation and *ATF2* Expression

US 7,569,380 B2

SIMULTANEOUS ANAEROBIC PRODUCTION OF ISOAMYL ACETATE AND SUCCINIC ACID

PRIOR RELATED APPLICATIONS

This application claims the benefit of U.S. Provisional Application Ser. No. 60/638,765 filed Dec. 22, 2004, entitled "Simultaneous Anaerobic Production of Isoamyl Acetate and Succinic Acid," which is incorporated herein in its entirety.

FEDERALLY SPONSORED RESEARCH STATEMENT

This invention may have been partially funded by grants from the National Science Foundation and/or The US Department of Agriculture. The government may have certain rights in the invention.

REFERENCE TO MICROFICHE APPENDIX

Not applicable.

FIELD OF THE INVENTION

An innovative in vivo method of producing esters from acetyl CoA, such as isoamyl acetate and succinate, has been developed by producing null mutants in pathways that use acetyl CoA and by overexpressing products that use NADH and in order to maintain the proper redox balance between NADH and NAD+. The method is exemplified with null mutations in ldhA, adhE, ackA-pta and overexpression of pyruvate carboxylase and alcohol acetyltransferase. This strain produces higher levels of both isoamyl acetate and succinate.

BACKGROUND OF THE INVENTION

Metabolic engineering incorporates a variety of academic disciplines to generate high production systems for desired, and largely commercial, products. Many of these products are expensive to produce because the downstream processing and purification is often very complex. High value products such as succinate, ethanol, and lactate are produced from glucose in *Escherichia coli* via the anaerobic central metabolic pathway. Additionally, heterologous genes are often expressed in *E. coli* to produce valuable compounds such as polyketides, nutritional compounds, and pigments.

To practice metabolic engineering, the physiology of the species must be understood to determine which manipulations to pursue. Manipulations necessary for a desired product(s) must be chosen systematically and accurately. Deleting certain pathways may be fatal to the cell, while deleting others may lead to a metabolic bottleneck and shortage of immediate metabolites necessary for the desired product. Understanding these manipulations to maximize production and reduce metabolic burden on the host cell is very important.

Recent work has been done to metabolically engineer *E. coli* to produce isoamyl acetate, a compound in the ester family (2, 10, 19, 20, 21). Isoamyl acetate is a valuable chemical used as an industrial solvent, plasticizer, cleaner, and a solvent for lacquer coatings and nail polish. However, its most important use is in the food industry where 74,000 kg/year are used (7), largely because it is a key element in the flavor of sake.

Two alcohol acetyltransferases (ATF1 and ATF2) in *Saccharomyces cerevisiae* were found to produce isoamyl acetate from acetyl-CoA and isoamyl alcohol during the yeast fermentation process in sake wine as well as other wines and beers (3, 15, 23, 24). Several constructs expressing ATF2 on a high-copy number plasmid were prepared and used in our laboratory for microbial, normative production of the ester in *E. coli* (19, 20).

While most focus has been on producing isoamyl acetate aerobically, pathway manipulations have also been applied to increase isoamyl acetate production anaerobically (21). As seen in FIG. 1, the ethanol (adhE) and acetate (ackA-pta) production pathways compete directly with the ester pathway for the precursor acetyl-CoA. Additionally, the lactate (ldhA) and succinate pathways compete indirectly with the ester pathway for the precursor pyruvate. Anaerobic cultures of a strain with a mutation in ackA-pta, thereby eliminating acetate production, produced more ester than the parent strain, demonstrating the positive effect of channeling carbon flux away from acetate production. However, eliminating lactate production with an additional mutation in ldhA resulted in a surprising drop in ester production. The cells must always maintain a proper redox balance between the cofactor pair NADH and $NAD^+$, and therefore the ethanol production pathway was restored, diverting carbon flux from ester production.

Another strategy for producing large amounts of isoamyl acetate anaerobically is to overexpress the succinate-producing pathway and eliminate the ethanol-producing pathway. Because the volatility of isoamyl acetate and succinate differs greatly, the two could be easily separated in an industrial setting. By employing this strategy, the cells remain healthy with a proper redox balance, and in the process two valuable and easily separated compounds are produced.

Succinate is valuable as a precursor to numerous products in the pharmaceutical and chemical industries (9). Two major pathways produce succinate (FIG. 1). The fermentative pathway anaerobically converts OAA to malate, fumarate, and finally succinate, reducing 2 moles of NADH (17). Aerobically, the glyoxylate pathway converts 2 moles of acetyl-CoA and 1 mole of OAA to 1 mole each of succinate and malate (12), which can be further converted to succinate via the pathway described above.

SUMMARY OF THE INVENTION

Previous attempts at producing the ester isoamyl acetate anaerobically did not produce the compound in high concentrations due to competing pathways and the need for $NAD^+$ regeneration. The objective of this work was to produce succinate in order to balance the ratio of $NADH/NAD^+$ as a way of maximizing isoamyl acetate production. Because the volatility of the two compounds differs greatly, the two could be easily separated in an industrial setting.

An ldhA, adhE double mutant strain served as the control strain to test the effect of an additional ackA-pta mutation. Both strains overexpressed the two heterologous genes pyruvate carboxylase (for maximal succinate production) and alcohol acetyltransferase (for ester production). Experiments varied temperature, sampling time, and substrate concentration to both test the feasibility of the system as well as to determine the conditions for maximal production of the two compounds.

The ldhA, adhE, ackA-pta strain (SBS990MG) was found to produce higher levels of both isoamyl acetate and succinate. At the optimal condition of 25° C., grown for 24 hours in LB media containing 10 mM isoamyl alcohol, the culture produced 9.4 mM isoamyl acetate and 45.5 mM succinate. The culture grown for 48 hours produced higher levels of both—9.95 mM isoamyl acetate and 51.8 mM succinate—but the glucose consumption was also much higher, resulting in lower molar yields. SBS990MG produced 36% more ester and over 7 times more succinate than SBS110MG when grown at 25° C. and sampled 24 hours after inoculation.

In addition to pathway manipulation, culture temperature was found to have a positive effect on production of both compounds. SBS990MG produced 28% more succinate and 75% more isoamyl acetate at 25° C. than at 37° C. in 24 hours.

DETAILED DESCRIPTION OF THE INVENTION

Figure 1:
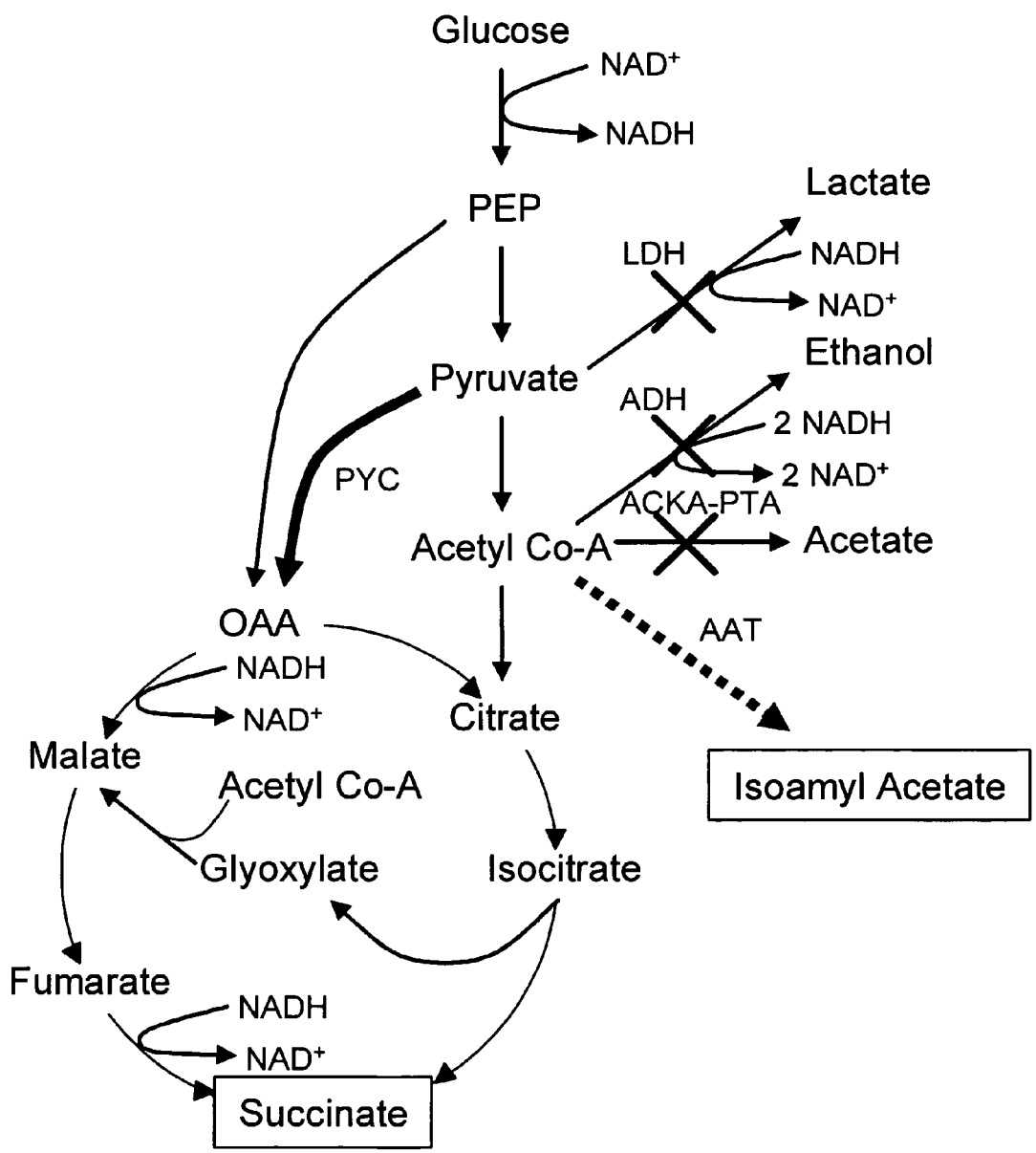
FIG. 1: Central anaerobic metabolic pathway of *E. coli* including the newly added isoamyl acetate production pathway.

The objective of this study was to utilize succinate production as a way of maintaining the proper redox balance between NADH and $NAD^+$ while maximizing isoamyl acetate production. An adhE, idhA double mutant served as the parent strain to compare with an adhE, ldhA, ackA-pta triple mutant. The ackA-pta acetate-producing pathway has been widely shown to reduce recombinant protein production. In addition to a loss of carbon and therefore an economic sink, acetate is also detrimental because it inhibits cell growth (6, 8, 14). The work identified the effects of temperature, sampling time, and substrate concentration on production of the two valuable compounds.

Carboxylic acids described herein can be a salt, acid, base, or derivative depending on structure, pH, and ions present. For example, the terms "succinate" and "succinic acid" are used interchangeably herein. Succinic acid is also called butanedioic acid ($C_4H_6O_4$). Chemicals used herein include formate, glyoxylate, lactate, malate, oxaloacetate (OAA), phosphoenolpyruvate (PEP), and pyruvate. Bacterial metabolic pathways including the Krebs cycle (also called citric acid, tricarboxylic acid, or TCA cycle) can be found in Principles of Biochemistry, by Lehninger as well as other biochemistry texts.

Isoamyl acetate ($C_7H_{14}O_2$), also called banana oil, is a colorless liquid used in flavorings, perfumery, and as a solvent. Isoamyl acetate is also referred to as acetic acid 3-methylbutyl ester, Isopentyl ethanoate, and pear oil, among other synonyms.

The terms "operably associated" or "operably linked," as used herein, refer to functionally coupled nucleic acid sequences.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like. By "null mutant" or "null mutation" what is meant is that the mutation produces less than 75% of the enzymatic activity of the wild type. Preferably, the activity is reduced 80-100%.

"Overexpression" or "overexpressed" is defined herein to be at least 150% of protein activity as compared with an appropriate control species. Preferably, the activity is increased 100-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like.

The terms "disruption" and "disruption strains," as used herein, refer to cell strains in which the native gene or promoter is mutated, deleted, interrupted, or down regulated in such a way as to decrease the activity of the gene. A gene can be completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

The term "exogenous" indicates that the protein or nucleic acid is introduced from or produced outside the organism or system. An exogenous peptide may be applied to the cell culture. An exogenous RNA may be expressed from a recombinant DNA transfected into a cell or may be a recombinant DNA from within a cell.

As used herein "recombinant" is relating to, derived from, or containing genetically engineered material.

Genes are abbreviated as follows: isocitrate lyase (aceA a.k.a. icl); malate synthase (aceB); the glyoxylate shunt operon (aceBAK); isocitrate dehydrogenase kinase/phosphorylase (aceK); acetate kinase-phosphotransacetylase (ackA-pta); acetyl-CoA synthetase (acs); alcohol dehydrogenase (adhE); aerobic respiratory control regulator A and B (arcAB); peroxide sensitivity (arg-lac); alcohol acetyltransferases 1 and 2 (atf1 and atf2); putative cadaverine/lysine antiporter (cadR); citrate synthase (citZ); fatty acid degradation regulon (fadR); fumarate reductase (frd); fructose regulon (fruR); fumarase A, B, or C (fum or fumABC); galactose permease (galP); citrate synthase (gltA); isocitrate dehydrogenase (icd); isocitrate lyase (icl); aceBAK operon repressor (iclR); lactate dehydrogenase (idhA); malate dehydrogenase (mdh); phosphoenolpyruvate carboxylase (pepC); pyruvate formate lyase (pfl); pyruvate oxidase (poxB); phosphotransferase system genes F and G (ptsF and ptsG); and pyruvate carboxylase (pyc). PYC can be derived from various species, *Lactococcus lactis pyc* is expressed as one example (AF068759).

Abbreviations: ampicillin (Ap); oxacillin (Ox); carbenicillin (Cn); chloramphenicol (Cm); kanamycin (Km); streptomycin (Sm); tetracycline (Tc); nalidixic acid (Nal); erythromycin (Em); ampicillin resistance ($Ap^R$); thiamphenicol/chloramphenicol resistance ($Thi^R/Cm^R$); macrolide, lincosamide and streptogramin A resistance ($MLS^R$); streptomycin resistance ($Sm^R$); kanamycin resistance ($Km^R$); Gram-negative origin of replication (ColE1); and Gram-positive origin of replication (OriII). Common restriction enzymes and restriction sites can be found at NEB® (NEW ENGLAND BIOLABS®, www.neb.com) and INVITROGEN® (www.invitrogen.com). ATCC®, AMERICAN TYPE CULTURE COLLECTION (www.atcc.org).

Plasmids and strains used in certain embodiments of the invention are set forth in Tables 1 and 2.

TABLE 1

PLASMIDS

| Plasmid | Genotype | Ref |
|---|---|---|
| pTrc99A | Cloning vector $Ap^R$ | 1 |
| pDHK29 | Cloning vector $Km^R$ | 16 |
| pHL413 | L. lactis pyc in pTrc99A, $Ap^R$ | 13 |
| pKmAT | atf2 with lac and ptb promoters, $Km^R$ | 19 |

TABLE 2

STRAINS

| Plasmid | Genotype | Ref |
|---|---|---|
| SBS110MG | MG1655 ΔadhE ldhA, $Km^S$ | 18 |
| SBS990MG | MG1655 ΔadhE ldhA ackA-pta::$Cm^R$ | 18 |

LB broth medium supplemented with 20 g/L of glucose, 1 g/L ampicillin, and 100 g/L kanamycin was used for all cultivations. 1 g/L of $NaHCO_3$ was added to the broth when used for anaerobic cultivations to reduce the initial lag time. Expression of pyruvate carboxylase and alcohol acetyltransferase was induced by the addition of isopropyl-β-thiogalactopyranoside (IPTG) to a final concentration of 1 mM.

For inoculum preparation, cells were grown aerobically in a 250 ml shake flask containing 50 ml of LB medium with appropriate antibiotic concentration at 37° C. and 250 rpm for 12 hours. Cells were harvested by centrifugation and resuspended in 50 ml of aerobic medium. The resuspended cells were transferred aseptically into a 2 L shake flask containing 350 ml of LB medium with appropriate antibiotic concentration at 37° C. and 250 rpm for 12 hours. Cells were harvested by centrifugation and resuspended in anaerobic medium to final concentration of either 10 $OD_{600}$ or 1 $OD_{600}$. Due to its volatile nature, isoamyl alcohol was added to the resuspended cells, rather than the LB broth, at a concentration of 0, 10, or 20 mM. A volume of 18 ml resuspended culture was then transferred to each 40 ml amber-colored tube, which contained 0.3 g of $MgCO_3$. Each tube was capped with a rubber septum and purged with sterile $CO_2$ at 1 L/min STP for 8 sec. The cultures were grown in a rotary shaker at either 25° C. or 37° C. and 250 rpm. Samples of the media and headspace gas were taken after 24 and/or 48 hr and analyzed for isoamyl acetate and metabolite production.

A 1 ml sample of cell culture broth was centrifuged at 8000 g for 3 min. The supernatant was filtered through a 0.45 μm syringe filter for HPLC analysis and stored frozen until analyzed. Metabolites such as residual glucose, acetate, ethanol, lactate, and pyruvate were quantified using an HPLC system (SHIMADZU-10A™ systems, SHIMADZU™, Columbia, Md.) equipped with a cation-exchange column (HPX-87H™, BIO-RAD™ Labs; Hercules, Calif.), a UV detector (SHIMADZU SPD-10A™) and a refractive index detector (WATERS 2410™, WATERS™, Milford, Mass.). Pyruvate was quantified using a UV detector, and the other metabolites using a refractive index detector. A 2.5 mM $H_2SO_4$ solution was used as mobile phase at a flow rate of 0.6 ml/min. The HPLC column was operated at 55° C.

Isoamyl acetate was determined by headspace gas chromatography, a protocol modified from Vadali, et al. (21). The flask was heated at 75° C. for 30 minutes and 1 ml of headspace gas was injected via a gas-tight syringe into a HEWLETT-PACKARD™ 6000 series gas chromatograph equipped with an ALLTECH™ 6'×¼"×2 mm POROPAK™ QS 80/100 column at a static temperature of 220° C. for 25 minutes. The injector and detector temperatures were 215° C. and 245° C. respectively. A 6% ethyl acetate solution was used as an internal standard to correct for pressure differences.

Effect of ack-pta on Isoamyl Acetate Production

Previously we have observed that deleting the acetate-producing ackA-pta pathway leads to an increase in anaerobic isoamyl acetate production (21). However, an additional mutation in the lactate-producing ldhA pathway reduced isoamyl acetate production to that of the wild type strain. Additionally, the ldhA deletion activated the adhE pathway, presumably because the strain must still maintain the proper redox balance between NADH and NAD+.

This study diverted the NADH recycling power away from ethanol production to succinate production in order to balance the cofactors, resulting in a healthier strain which produced higher levels of isoamyl acetate. We constructed two strains which overexpressed alcohol acetyltransferase (ATF2) for isoamyl acetate production, and pyruvate carboxylase (PYC) for increased flux to OAA for succinate production.

In previous works, PYC was shown to increase both the succinate production and yield (4, 5, 17, 22). SBS110MG (MG1655 adhE ldhA) served as the control strain and SBS990MG (MG1655 adhE ldhA ackA-pta) served as the experimental strain to determine the effect of an ackA-pta mutation on isoamyl acetate and succinate production. Both strains carried the two plasmids pHL413 and pKmAT.

Reducing the competing pathways for acetyl-CoA by deleting ackA-pta led to a significant increase in isoamyl acetate production. FIG. 3a shows levels of isoamyl acetate production for cultures of strains SBS110MG (pHL413, pKmAT) and SBS990MG (pHL413, pKmAT), 24 and 48 hours after inoculation, grown at either 25° C. or 37° C. The highest level of ester production (9.95 mM) was seen in SBS990MG (pHL413, pKmAT), 48 hours after inoculation, grown at 25° C. When supplemented 10 mM isoamyl alcohol, this culture produced the theoretical maximum ester yield, because 1 mole of isoamyl alcohol is needed for every mole of isoamyl acetate produced. Under these conditions, SBS990MG (pHL413, pKmAT) produced 32% more isoamyl acetate than SBS110MG (pHL413, pKmAT) did. Additionally, SBS990MG (pHL413, pKmAT) produced 36% more ester than SBS110MG (pHL413, pKmAT) after 24 hours, generating 9.41 mM. However, because cultures of SBS990MG consumed much more glucose than did cultures of SBS110MG (FIG. 2) the molar yields of isoamyl acetate were lower (FIG. 3b).

Culturing temperature also had a large effect on isoamyl acetate production. As seen in a previous study (19), lower temperatures lead to an increase in ester concentration. SBS990MG (pHL413, pKmAT) produced 75% more ester at 25° C. than at 37° C. after 24 hours, and 64% more after 48 hours.

Figure 2:
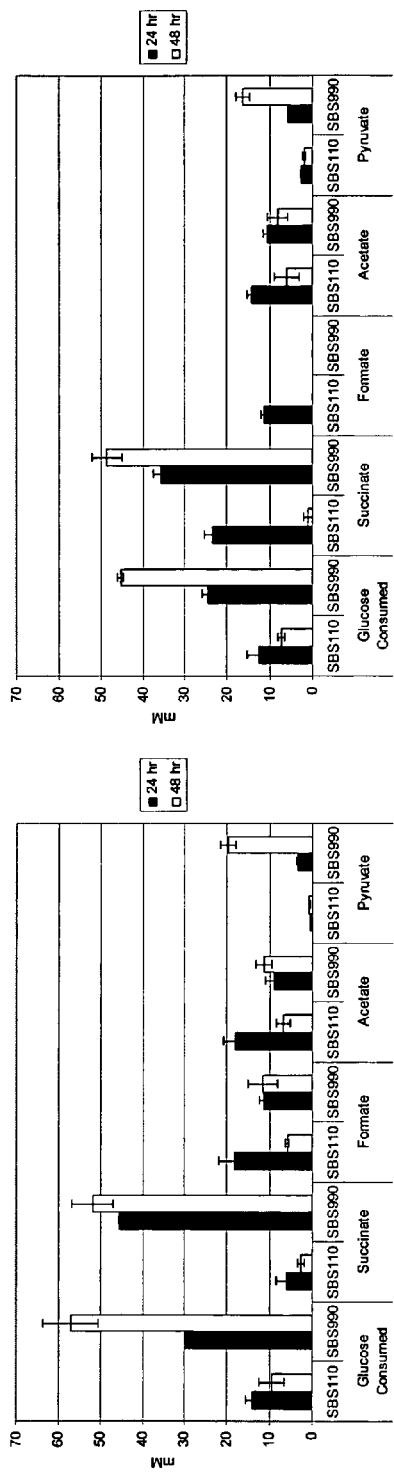
FIGS. 2a-2d: Extracellular metabolite production and molar yields of SBS110MG (pHL413, pKmAT) and SBS990MG (pHL413, pKmAT). The data shown are means +/−standard deviation for triplicate experiments.
Figure 2:
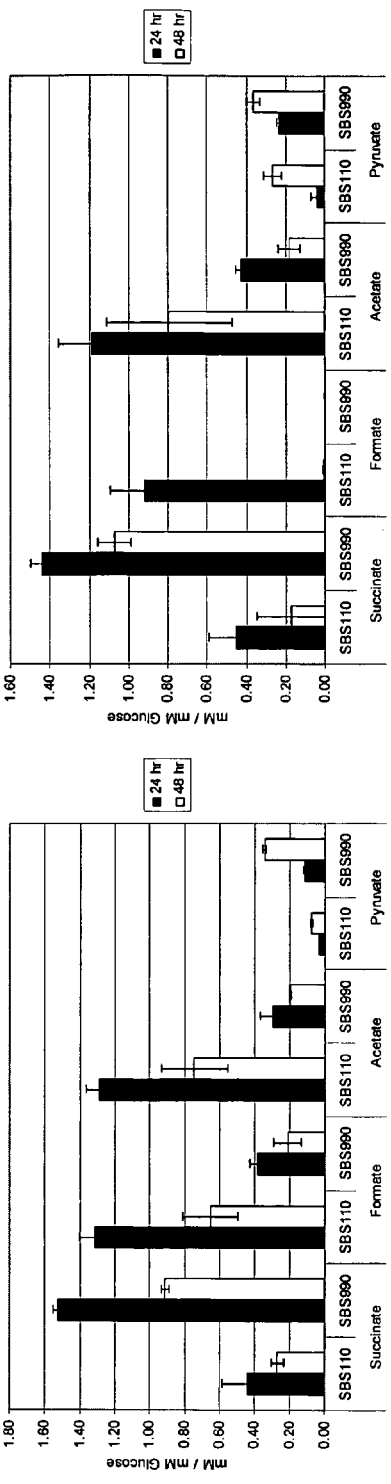
Figure 3:
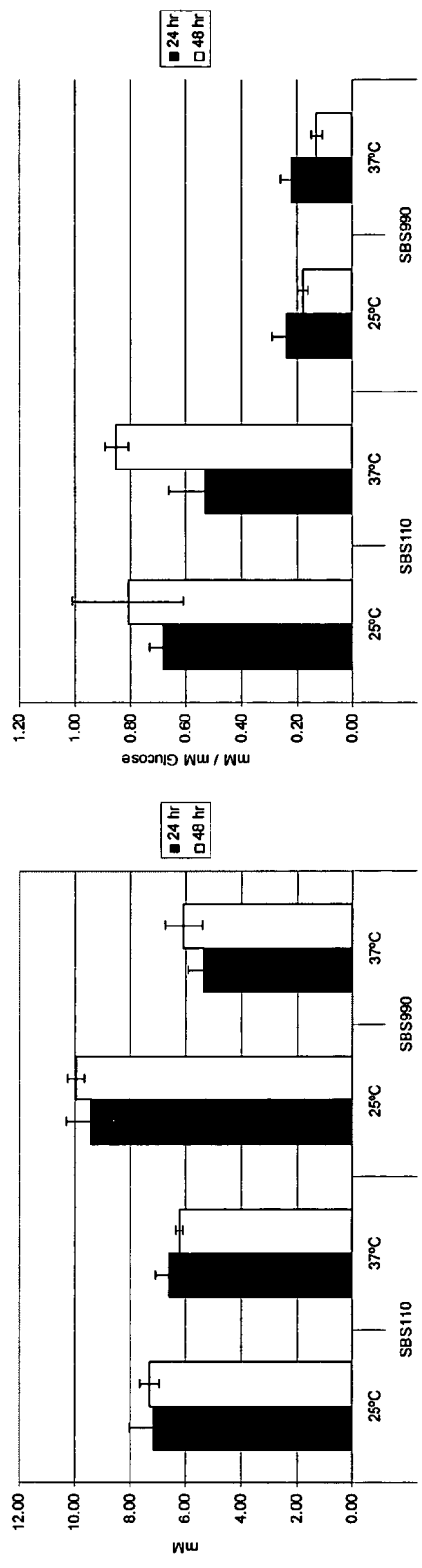
FIGS. 3a-3b: Isoamyl acetate production (a) and yield (b) of SBS110MG (pHL413, pKmAT) and SBS990MG (pHL413, pKmAT). The data shown are means +/−standard deviation for triplicate experiments.

As seen in FIG. 2, the additional ackA-pta deletion led to a dramatic increase in succinate production in cultures of SBS990MG (pHL413, pKmAT), when compared to SBS110MG (pHL413, pKmAT). This increase was seen at both 25° C. and 37° C., and also at both sampling times (24 and 48 hr). At 25° C., SBS990MG (pHL413, pKmAT) produced over 7-fold more succinate than cultures of SBS110MG (pHL413, pKmAT) after 24 hours, and over 20-fold after 48 hours.

An increase in total succinate was observed after 48 hours when compared to 24 hours. SBS990MG (pHL413, pKmAT) cultures produced 36% more succinate after 48 hours than after 24 hours when grown at 37° C. When cultures were grown at 25° C., a 14% increase was observed. However, the molar succinate yields (mol succinate/mol glucose) for the culture of SBS990MG (pHL413, pKmAT) dropped after 24 hours because of the large amount of glucose consumed in the second 24 hour period. Lower culturing temperature also had a positive effect on succinate production. At the 24 hour time point, the SBS990MG (pHL413, pKmAT) culture produced 28% more succinate at 25° C. than at 37° C.

In addition to altering succinate and ester production, pathway manipulation, culturing temperature, and sampling time also had an effect on other extracellular metabolites including acetate, formate, and pyruvate. As seen in FIG. 2, the SBS990MG (pHL413, pKmAT) culture consumed significantly more glucose than SBS110MG (pHL413, pKmAT) at both temperatures and sampling times. However, the OD600 of the SBS990MG (pHL413, pKmAT) culture was slightly less than that of SB110MG (pHL413, pKmAT) (data not shown).

While the acetate production of cultures of the two strains was relatively equivalent, the figures (2c, 2d) show that the molar acetate yield of SBS990MG (pHL413, pKmAT) was much less than that of SBS110MG (pHL413, pKmAT). Residual formate levels in cultures of SBS110MG (pHL413, pKmAT) were higher than found with SBS990MG (pHL413, pKmAT). Formate was excreted as part of the pyruvate formate lyase (PFL) pathway from pyruvate to acetyl-CoA. With the ack-pta pathway intact in SBS110MG (pHL413, pKmAT), the carbon flux through the PFL pathway was greater than in SBS990MG (pHL413, pKmAT) when the flux was shifted to the PEPC and PYC pathways. In contrast, SBS990MG (pHL413, pKmAT) exhibited a larger amount of pyruvate leakage than SBS110MG (pHL413, pKmAT). The PYC and ester producing pathways were likely not strong enough to fully utilize the pyruvate pool, and therefore the excess was excreted into the broth. The pyruvate continued to accumulate after 24 hours.

Figure 4:
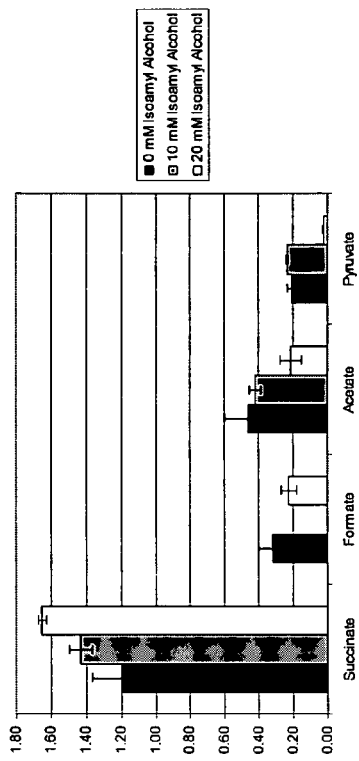
FIGS. 4a-4b: Extracellular metabolite production (4a) and yields (4b) of SBS990MG (pHL413, pKmAT) with different quantities of isoamyl alcohol. Cultures were supplemented with 0, 10, or 20 mM isoamyl alcohol and grown at 25° C. for 24 hours. The data shown are means+/−standard deviation for triplicate experiments.
Figure 4:
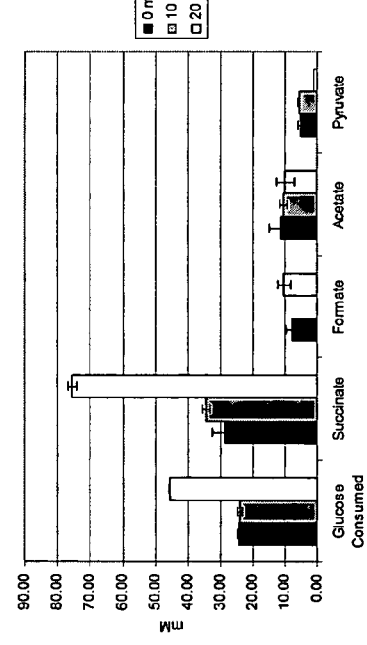
Figure 5:
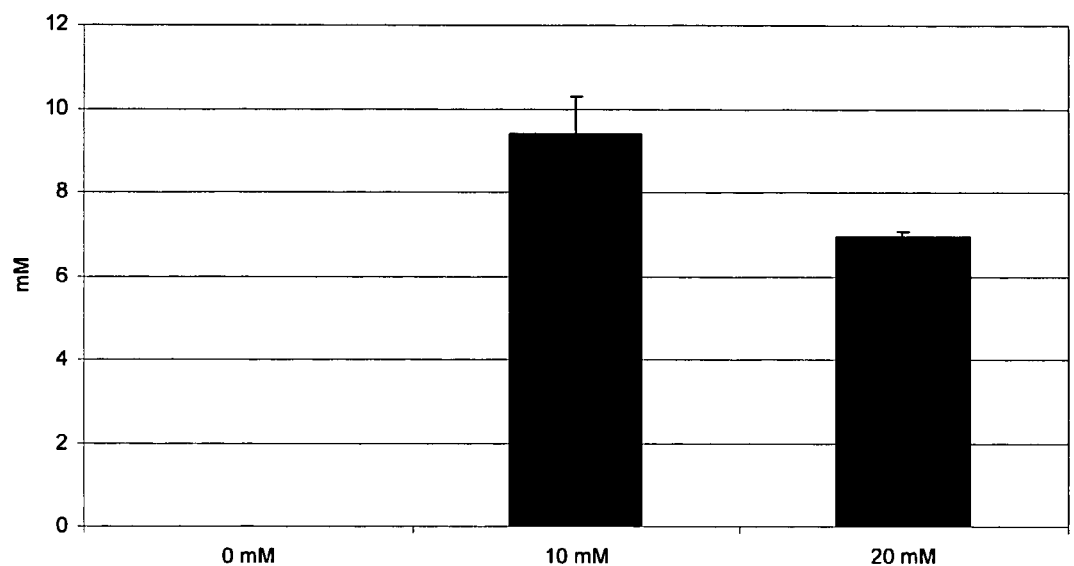
FIG. 5: Isoamyl acetate production of SBS990MG (pHL413, pKmAT), supplemented with 0, 10, or 20 mM isoamyl alcohol. Cultures were supplemented with 0, 10, or 20 mM isoamyl alcohol and grown at 25° C. for 24 hours. The data shown are means+/−standard deviation for triplicate experiments.
Figure 6:
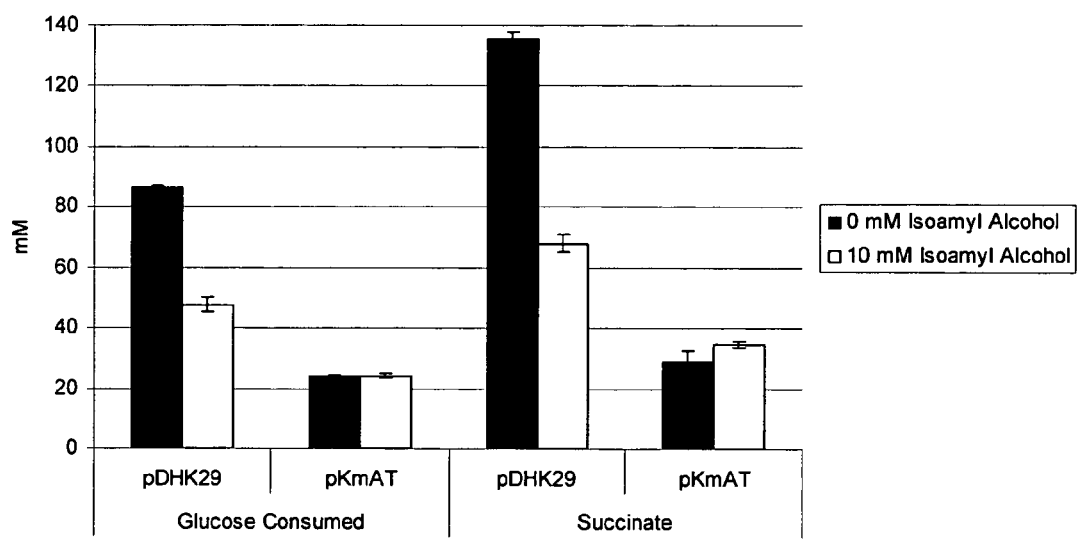
FIG. 6: Effect of isoamyl alcohol and ATF2 expression on glucose consumption and succinate production. SBS990MG (pHL413, pDHK29) and SBS990MG (pHL413, pKmAT) cultures supplemented with 0, 10, or 20 mM isoamyl alcohol and grown at 37° C. for 24 hours. The data shown are means +/−standard deviation for triplicate experiments.

Because SBS990MG (pHL413, pKmAT) grown at a temperature of 25° C. and sampled at 24 hours reached the theoretical maximum production of isoamyl acetate, the amount of the substrate isoamyl alcohol was increased from 10 mM to 20 mM. As seen in FIG. 4, the absolute succinate production as well as the molar yield increased due to the addition of supplemental isoamyl alcohol. In addition, the succinate production and molar yield both decreased when no isoamyl alcohol was added when compared to 10 mM. The fitness of the cells also appeared to increase with the addition of 20 mM isoamyl alcohol, because the amount of glucose consumed was substantially higher than that of 0 mM or 10 mM isoamyl alcohol. While the succinate production was significantly higher with 20 mM isoamyl alcohol, the production of isoamyl acetate decreased (FIG. 5). Previous research had shown that the addition of isoamyl alcohol lead to almost a three-fold increase in the specific activity of succinate dehydrogenase, the enzyme responsible for the interconversion of fumarate and succinate (11). Perhaps the system shifted to succinate production and away from isoamyl acetate production under such conditions.

The final experiment compared the effect of ATF2 expression with a control plasmid, pDHK29, combined with the strain SBS990MG (pHL413). As seen in FIG. 5, pKmAT presented a burden to the strain, limiting glucose consumption as well as decreasing succinate production. Furthermore, the strain SBS990MG (pHL413, pDHK29) was greatly affected by the addition of isoamyl alcohol. Glucose consumption and succinate production both decreased as a result of the presence of isoamyl alcohol. However, SBS990MG (pHL413, pKmAT) appeared largely unaffected by the addition of isoamyl alcohol. Both glucose consumption and succinate levels remained relatively constant. Perhaps ester formation could be a way for the cells to avoid the problem of alcohol inhibition.

This study accomplished the simultaneous production of two easily-separable compounds isoamyl acetate and succinate in *E. coli*. The succinate pathway was used to maintain the proper redox balance between NADH and NAD+ to allow for higher levels of isoamyl acetate production. Additionally, this study aimed to test pathway mutation, culture temperature, sampling time, and substrate concentration.

A culture of a strain lacking all major competing pathways (adhE ldhA ackA-pta) was found to produce higher levels of both high value compounds than a culture of the control strain which still had the ackA-pta pathway intact. Both strains overexpressed the two heterologous genes pyruvate carboxylase (for maximal succinate production) and alcohol acetyltransferase (for ester production). The optimal condition for high molar yield was found to be 25° C. with samples taken 24 hours after inoculation. Lower temperatures maximized production of both compounds and the shorter sampling time allowed for higher yields. In addition, excess isoamyl alcohol led to more succinate production but less ester production perhaps because it increased the specific activity of succinate dehydrogenase. Under optimal conditions, cultures of SBS990MG (pHL413, pKmAT) produced 9.4 mM isoamyl acetate and 45.5 mM succinate, 36% more isoamyl acetate and over 7 times more succinate than cultures of SBS110MG (pHL413, pKmAT) grown under the same conditions.

REFERENCES

All references are listed herein for the convenience of the reader. Each is incorporated by reference in its entirety.

1. Amann, et al., "Tightly regulated tac promoter vectors useful for the expression of unfused and fused proteins in *Escherichia coli*," Gene 69:301-15 (1988).
2. Dittrich, et al., "Redistribution of metabolic fluxes in the central aerobic metabolic pathway of *E. coli* mutant strains with deletion of the ackA-pta and poxB pathways for the production of isoamyl acetate," Biotechnol. Prog. 21:627-31 (2005).
3. Fujii, et al., "Molecular cloning, sequence analysis, and expression of the yeast alcohol acetyltransferase gene," Appl. Environ. Microbiol. 60:2786-2792 (1994).
4. Gokarn, et al., "Expression of pyruvate carboxylase enhances succinate production in *E. coli* without affecting glucose uptake rate," Biotech. Let. 20:795-8 (1998).
5. Gokarn, et al., "Metabolic analysis of *E. coli* in the presence and absense of the carboxylating enzymes phospho- 6. Hahm, et al., "Characterization and evaluation of a pta (phosphotransacetylase) negative mutant of *E. coli* HZB11 as a production host of foreign lipase," Appl. Microbiol. Biotechnol. 42:100-7 (1994).

7. Hari Krishna, et al., "Enzymatic synthesis of isoamyl acetate using immobilized lipase from *Rhizomucor miehei*," J. Biotechnol. 87:193-201 (2001).

8. Holms, "The central metabolic pathways in *E. coli*: relationship between flux and control at a branchpoint, efficiency of conversion to biomass, and excretion of acetate," Curr. Top. Cell Regul. 28:69-105 (1986).

9. Hong and Lee, "Importance of redox balance on the production of succinic acid by metabolically engineered *E. coli*," Appl. Microbiol. Biotechnol. 58:286-90 (2002).

10. Horton, et al., "Heterologous expression of the *Saccharomyces cerevisiae* alcohol acetyltransferase," J. Ind. Microbiol. Biotechnol. 30:427-32 (2003).

11. Kern, et al., "Isoamyl alcohol-induced morphological change in *Saccharomyces cerevisiae* involves increases in mitochondria and cell wall chitin content," FEMS Yeast Res. 5:43-9 (2004).

12. Kornberg, "The role and control of the glyoxylate cycle in *E. coli*," Biochem. J. 99:1-11 (1966).

13. Lin, et al., "Increasing the acetyl-CoA pool in the presence of overexpressed phosphoenolpyruvate carboxylase or pyruvate carboxylase enhances succinate production in *E. coli*," Biotech. Prog. 20:1599-604 (2004).

14. Luli and Strohl, "Comparison of growth, acetate production, and acetate inhibition of *E. coli* strains in batch and fed-batch fermentations," Appl. Environ. Microbiol. 56:1004-11 (1990).

15. Nagasawa, et al., "Cloning and nucleotide sequence of the alcohol acetyltransferase II gene (ATF2) from *Saccharomyces cerevisiae*," Biosci. Biotech. Biochem. 62:1852-7 (1998).

16. Phillips, et al., "High copy number plasmids compatible with commonly used cloning vectors," Biotechniques 28:400-8 (2000).

17. Sanchez, et al., "Efficient succinate production from glucose through overexpression of pyruvate carboxylase in an *E. coli* alcohol dehydrogense and lactate dehydrogenase mutant," Biotechnol. Prog. 21:358-65 (2005). [Submitted. 2004a].

18. Sanchez, et al., "Novel pathway engineering design of the anaerobic central metabolic pathway in *E. coli* to increase succinate yield and productivity," Metab. Eng. 7:229-39 (2005) [Submitted, 2004b].

19. Vadali, et al., "Applicability of CoA/acetyl-CoA manipulation system to enhance isoamyl acetate production in *E. coli*," Metab. Eng. 6:294-9 (2004a).

20. Vadali, et al., "Enhanced isoamyl acetate production upon manipulation of the acetyl-CoA node in *E. coli*," Biotech. Prog. 20:692-7 (2004b).

21. Vadali, et al., "Production of isoamyl acetate in ackA-pta and/or ldh mutants of *E. coli* with overexpression of yeast ATF2," Appl. Microbiol. Biotechnol. 63:698-704 (2004c).

22. Vemuri, et al., "Effect of growth mode and pyruvate carboxylase on succinic acid production by metabolically engineered strains of *E. coli*," Appl. Environ. Microbiol. 68:1715-27 (2002).

23. Yoshimoto, et al., "Isolation and classification of the ATF2 gene encoding alcohol acetyltransferase II in the bottom fermenting yeast *Saccharomyces pastorianus*," Yeast 15:409-17 (1999).

24. Yoshioka and Hashimoto, "Ester formation by alcohol acetyltransferase from brewers' yeast," Agric. Biol. Chem. 45:2183-90 (1981).

What is claimed is:

1. A metabolically engineered bacterial cell wherein said cell comprises:
   a) a disruption of the genes for lactate dehydrogenase (ldhA) and alcohol dehydrogenase (adhE) which results in decreased activity of lactate dehydrogenase (LDH) and alcohol dehydrogenase (ADH); and
   b) an expression vector encoding an exogenous alcohol acetyltransferase (ATF) and an exogenous pyruvate carboxylase (PYC).

2. The bacterial cell of claim 1, wherein said cell further comprises:
   a) decreased expression of a protein selected from the group consisting of aerobic respiratory control regulator A and B (ARCAB), peroxide sensitivity (ARG-LAC), putative cadaverine/lysine antiporter (CADR), fatty acid degradation regulon (FADR), fumarate reductase (FRD), fructose regulon (FRUR), fumarase (FUM), isocitrate dehydrogenase (ICD), isocitrate lyase (ICL), aceBAK operon repressor (ICLR), lactate dehydrogenase (LDH), malate dehydrogenase (MDH), pyruvate oxidase (POXB), phosphotransferase system genes (PTS), and succinate dehydrogenase (SDH); and
   b) overexpression of a protein selected from the group consisting of isocitrate lyase (ACEA), malate synthase (ACEB), isocitrate dehydrogenase kinase/phosphorylase (ACEK), citrate synthase (CITZ), phosphoenol pyruvate carboxylase (PEPC), and pyruvate formate lyase (PFL).

3. The bacterial cell of claim 1, wherein said cell further comprises decreased activity of one or more proteins selected from the group consisting of acetate kinase (ACK) and phosphotransacetylase (PTA).

4. The bacterial cell of claim 1, wherein said cell further comprises a disruption of the genes for acetate kinase (ack), phosphotransacetylase (pta), or acetate kinase-phosphotransacetylase (ack-pta).

5. The bacterial cell of claim 1, wherein said bacteria further comprises
   a disruption of the genes for, acetate kinase (ack) and phosphotransacetylase (pta).

6. A method of producing increased level of isoamyl acetate and succinate comprising:
   a) culturing an *E.coli* cell comprising:
      i) disruption of the genes for lactate dehydrogenase (ldhA) and alcohol dehydrogenase (adhE) which results in decreased activity of lactate dehydrogenase (LDH) and alcohol dehydrogenase (ADH);
      ii) an expression vector encoding an exogenous alcohol acetyltransferase (ATF) and an exogenous pyruvate carboxylase (PYC); and
   b) isolating isoamyl acetate, succinate, or both isoamyl acetate and succinate.

7. The method of claim 6, wherein said cell further comprises:
   a) decreased expression of a protein selected from the group consisting of aerobic respiratory control regulator A and B (ARCAB), peroxide sensitivity (ARG-LAC), putative cadaverine/lysine antiporter (CADR), fatty acid degradation regulon (FADR), fumarate reductase (FRD), fructose regulon (FRUR), fumarase (FUM), isocitrate dehydrogenase (ICD), isocitrate lyase (ICL), aceBAK operon repressor (ICLR), lactate dehydrogenase (LDH), malate dehydrogenase (MDH), pyruvate oxidase (POXB), phosphotransferase system genes (PTS), and succinate dehydrogenase (SDH); and b) overexpression of a protein selected from the group consisting of isocitrate lyase (ACEA), malate synthase (ACEB), isocitrate dehydrogenase kinase/phosphorylase (ACEK), citrate synthase (CITZ), phosphoenol pyruvate carboxylase (PEPC), and pyruvate formate lyase (PFL).

8. The method of claim 6, wherein said cell further comprises decreased activity of one or more proteins selected from the group consisting of acetate kinase (ACK) and phosphotransacetylase (PTA).

9. The method of claim 6, wherein said cell further comprises a disruption of the genes for acetate kinase (ack), phosphotransacetylase (pta), or acetate kinase-phosphotransacetylase (ack-pta).

10. The method of claim 6, wherein said cell is cultured at 25° C.

11. The method of claim 6, wherein said cell is cultured for 24 hours or less.

* * * * *

UNITED STATES PATENT AND TRADEMARK OFFICE
CERTIFICATE OF CORRECTION

PATENT NO. : 7,569,380 B2 Page 1 of 1
APPLICATION NO. : 11/315453
DATED : August 4, 2009
INVENTOR(S) : Ka Yui San et al.

It is certified that error appears in the above-identified patent and that said Letters Patent is hereby corrected as shown below:

Column 1, Lines 15 to 18 - Replace the sentences "This invention may have been partially funded by grants from the National Science Foundation and/or The US Department of Agriculture. The government may have certain rights in the invention." with -- This invention was made with government support under Grant Numbers BES-0000303 and BES-0118815 awarded by the National Science Foundation. The government has certain rights in the invention. --

Signed and Sealed this

Twenty-seventh Day of April, 2010

David J. Kappos
*Director of the United States Patent and Trademark Office*